US009101717B2

(12) United States Patent
Mansour et al.

(10) Patent No.: US 9,101,717 B2
(45) Date of Patent: Aug. 11, 2015

(54) NON-VENTED VIAL ACCESS SYRINGE

(71) Applicants: George Michel Mansour, Pomona, CA (US); Tyler Devin Panian, Long Beach, CA (US)

(72) Inventors: George Michel Mansour, Pomona, CA (US); Tyler Devin Panian, Long Beach, CA (US)

(73) Assignee: CAREFUSION 303, INC., San Diego, CA (US)

( * ) Notice: Subject to any disclaimer, the term of this patent is extended or adjusted under 35 U.S.C. 154(b) by 325 days.

(21) Appl. No.: 13/797,683

(22) Filed: Mar. 12, 2013

(65) Prior Publication Data

US 2014/0276386 A1 Sep. 18, 2014

(51) Int. Cl.
*A61J 1/20* (2006.01)
*A61M 5/31* (2006.01)
*A61M 5/315* (2006.01)

(52) U.S. Cl.
CPC ............... *A61M 5/31* (2013.01); *A61J 1/2096* (2013.01); *A61M 5/31511* (2013.01); *A61J 2001/2006* (2013.01); *A61J 2001/2072* (2013.01); *A61M 2005/3114* (2013.01); *A61M 2005/3121* (2013.01); *A61M 2005/3123* (2013.01)

(58) Field of Classification Search
CPC ........... A61J 1/20; A61J 1/202; A61J 1/2003; A61J 1/2068; A61J 1/2096
USPC .................... 141/21, 25–27, 52; 604/411–414
See application file for complete search history.

(56) References Cited

U.S. PATENT DOCUMENTS

| 4,660,569 A * | 4/1987 | Etherington .................. 600/578 |
| 5,007,919 A * | 4/1991 | Silva et al. ..................... 606/194 |
| 6,086,559 A * | 7/2000 | Enk ................................ 604/121 |
| 8,267,911 B2 * | 9/2012 | Gallogly et al. ............. 604/408 |
| 2011/0224611 A1 | 9/2011 | Lum et al. |
| 2014/0261876 A1 * | 9/2014 | Mansour et al. ................ 141/27 |

FOREIGN PATENT DOCUMENTS

| WO | 0100261 A1 | 1/2001 |
| WO | 2009029974 A1 | 3/2009 |

OTHER PUBLICATIONS

International Search Report and Written Opinion dated Jun. 11, 2014, for International Application No. PCT/US2014/018082.

* cited by examiner

*Primary Examiner* — Nicolas A Arnett
(74) *Attorney, Agent, or Firm* — McDermott Will & Emery LLP

(57) ABSTRACT

A syringe includes a plunger having a plunger tube with proximal and distal ends, a center tube with a center passage that extends within the plunger tube, and a balloon disposed over the center tube and sealingly fixed to at least one of the center tube and the plunger tube. The syringe also includes a barrel having a barrel tube having proximal and distal ends and an interior configured to accept a portion of the plunger, a tip fixedly coupled to the proximal end of the barrel tube, a post fixedly attached to the tip and extending within the barrel tube toward the distal end, the tip configured to partially extend into the center passage of the plunger, and a gas passage extending from a proximal end of the tip to the distal end of the post.

21 Claims, 4 Drawing Sheets

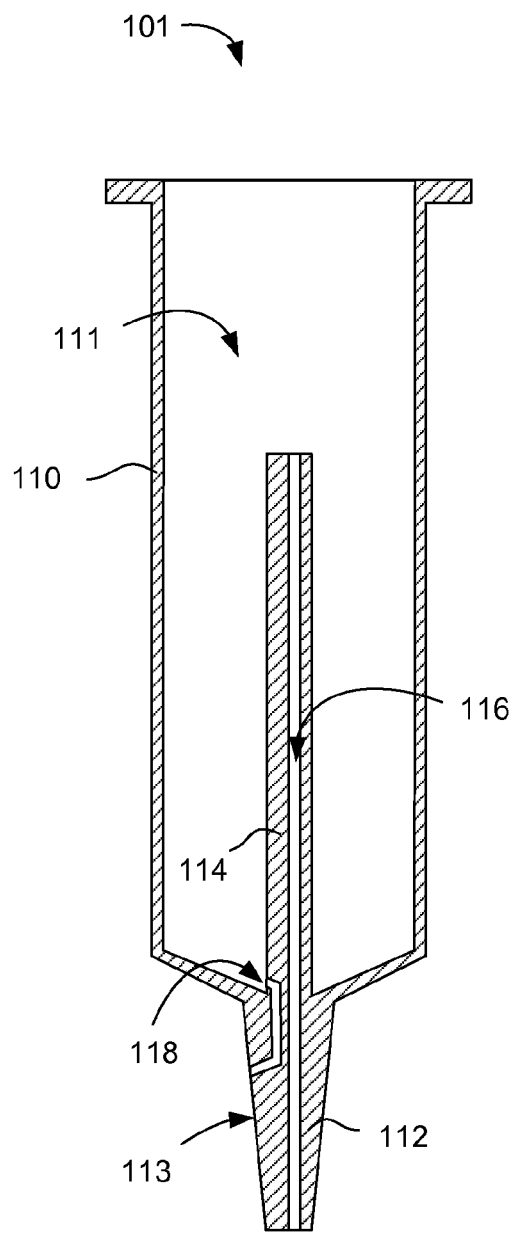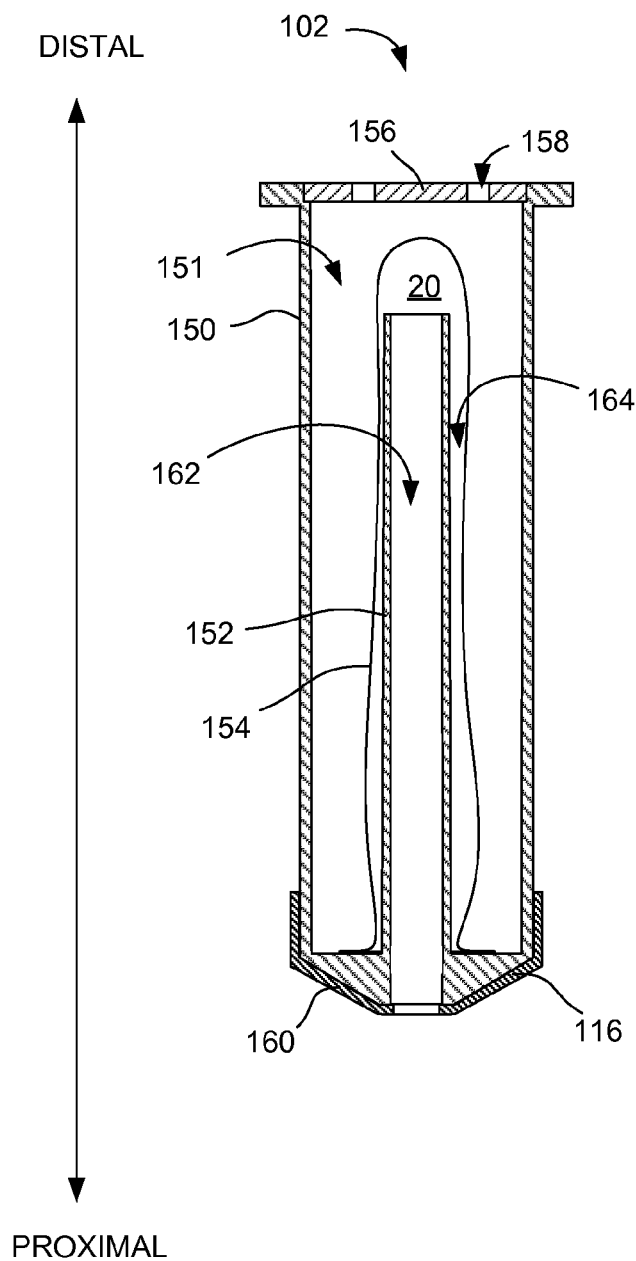
FIG. 1A
FIG. 1B

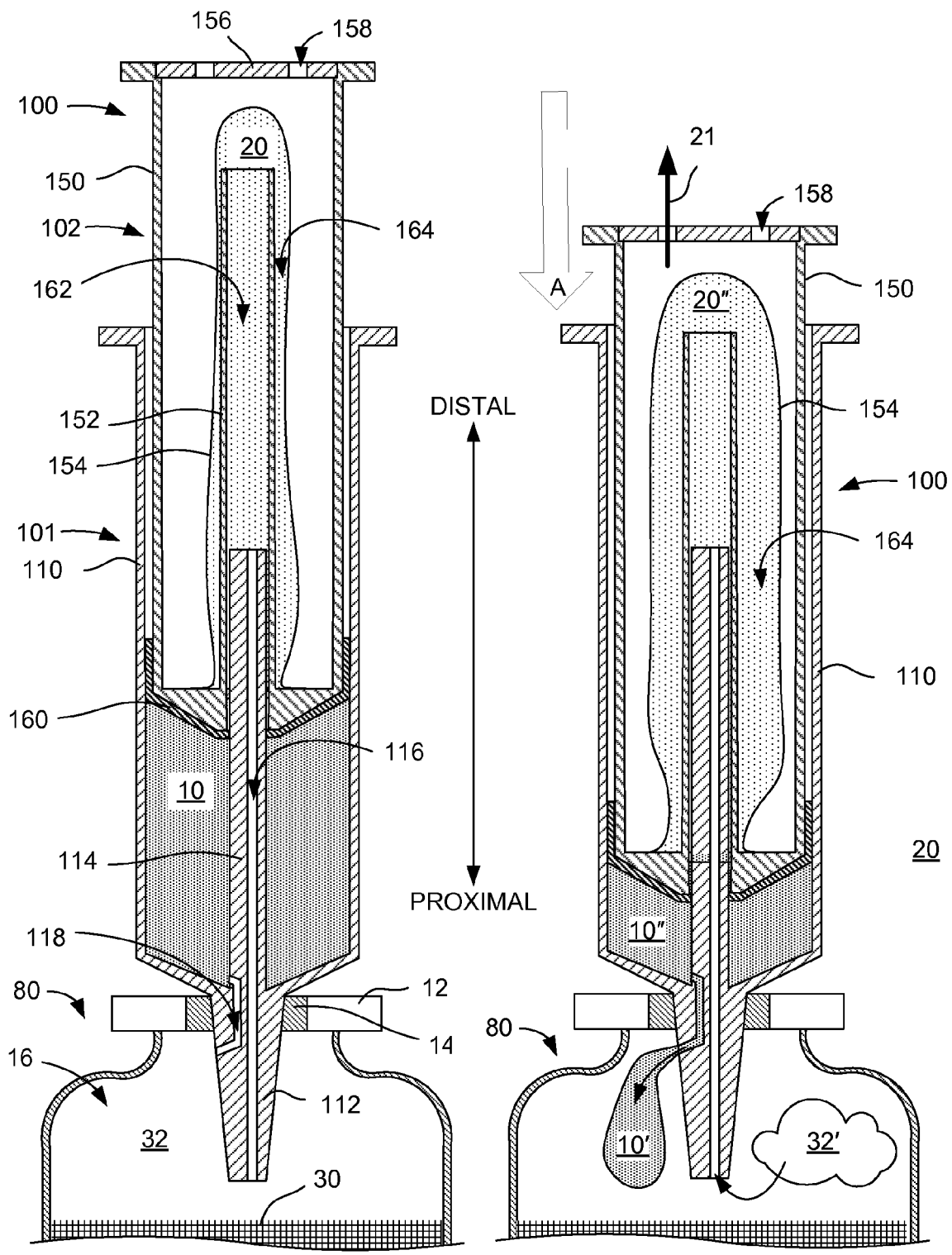
*FIG. 2A*     *FIG. 2B*

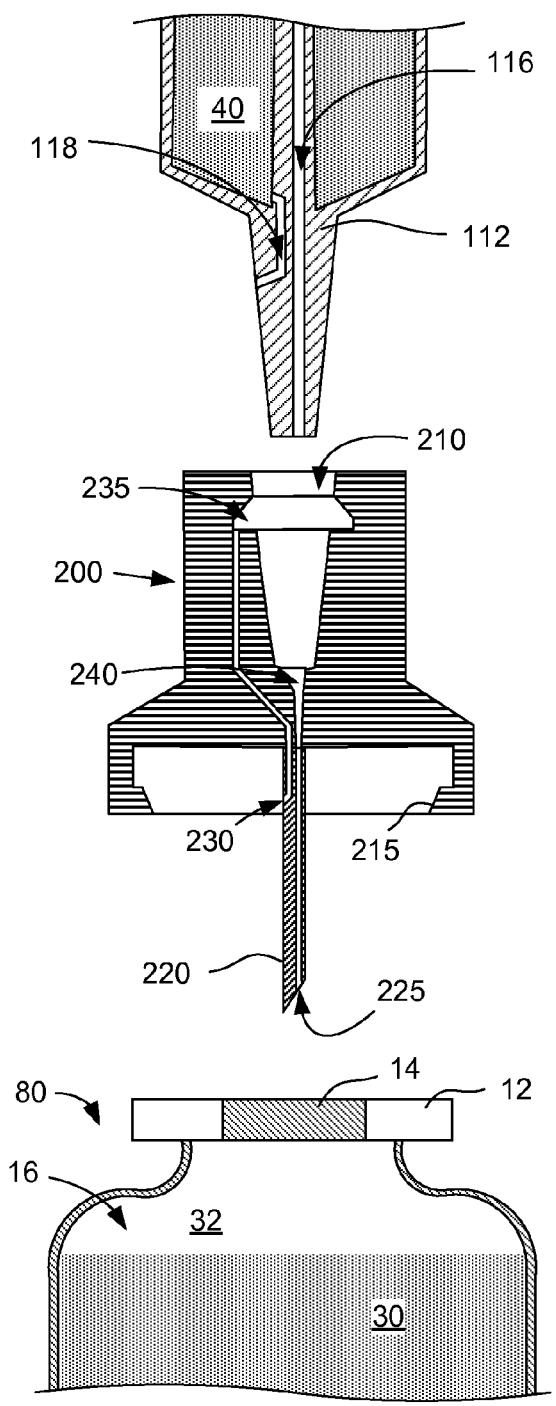
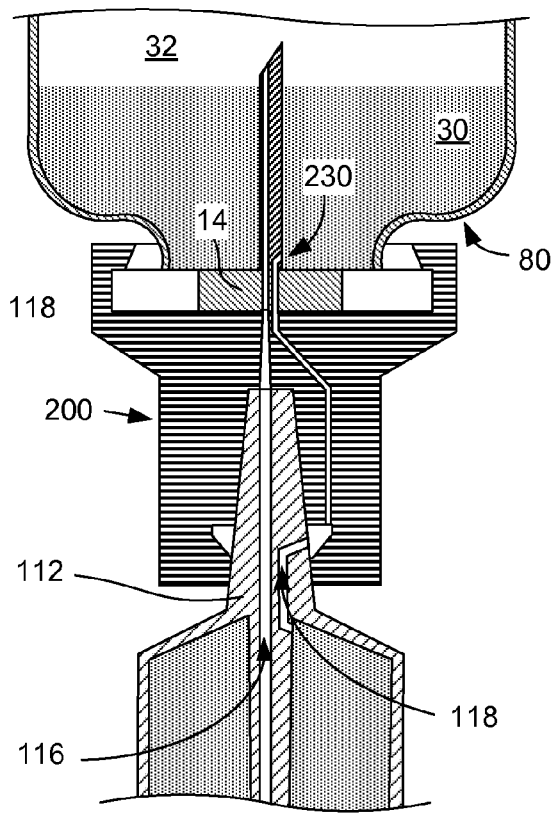
FIG. 4A
FIG. 4B

NON-VENTED VIAL ACCESS SYRINGE

CROSS-REFERENCES TO RELATED APPLICATIONS

Not applicable.

BACKGROUND

1. Field

The present disclosure generally relates to syringes and, in particular, to a syringe for extracting the contents of a sealed vial.

2. Description of the Related Art

Medications are often delivered in sealed vials. The medicine may be in either liquid form, and therefore ready to use, or in a dry, powdered form that requires reconstitution prior to use. In the case of a liquid medication, extraction of the liquid without introducing a gas into the vial results in a partial vacuum being created within the vial, which makes the extraction of the liquid more difficult. In the case of a dry medication, introduction of water into the vial, so as to reconstitute the medication, results in an increased pressure within the vial, which makes it difficult to introduce the water as well as presenting a hazard when extracting the reconstituted medication.

Vials are typically provided with a septum adapted for penetration by a needle. Vial adapters are available that include a needle, which is arranged to penetrate the septum of a vial, that is in fluid communication with a female needleless fitting configured to accept a needleless male fitting of a syringe. Common needleless fittings have a "Luer taper" conforming to an International Standards Organization (ISO) standard. Certain connectors have a self-sealing feature to prevent leakage of fluid from the attached vial when the syringe is decoupled from the fitting of the vial adapter. Certain vial adapters provide vent paths to the ambient environment to allow ambient air to enter the vial or allow gas to be expelled from the vial to the ambient environment. Certain vial adapters include a sealed chamber that capture gas expelled from the vial and prevent the expelled gas from passing into the ambient environment.

SUMMARY

The non-vented syringe disclosed herein is adapted for use with a sealed vial, in various embodiments, so as to maintain a generally constant pressure within the vial while adding or removing liquid.

In certain embodiments, a syringe is disclosed that includes a plunger having a plunger tube having proximal and distal ends, a center tube coupled to the proximal end of the plunger tube and extending within the plunger tube toward the distal end, the center tube having a center passage, and a balloon disposed over the center tube and sealingly fixed to at least one of the center tube and the plunger tube. The syringe also includes a barrel having a barrel tube having proximal and distal ends and an interior configured to accept a portion of the plunger, a tip fixedly coupled to the proximal end of the barrel tube, a post fixedly attached to the tip and extending within the barrel tube toward the distal end, the tip configured to partially extend into the center passage of the plunger, and a gas passage extending from a proximal end of the tip to the distal end of the post.

In certain embodiments, a pre-filled syringe is disclosed that contains a prefill volume of a medical fluid. The syringe includes a plunger having a plunger tube having proximal and distal ends, a center tube coupled to the proximal end of the plunger tube and extending within the plunger tube toward the distal end, the center tube having a center passage, and a balloon disposed over the center tube and sealingly fixed to at least one of the center tube and the plunger tube. The balloon and the at least one of the center tube and the plunger tube form a gas volume containing a gas. The syringe also includes a barrel having a barrel tube having proximal and distal ends and an interior configured to accept a portion of the plunger, a tip fixedly coupled to the proximal end of the barrel tube, a post fixedly attached to the tip and extending within the barrel tube toward the distal end, the tip configured to partially extend into the center passage of the plunger, and a gas passage extending from a proximal end of the tip to the distal end of the post. The plunger is partially inserted into the barrel so as to form a liquid volume that contains the prefill amount of the medical fluid. The balloon is able to further expand such that the gas volume increases by at least the prefill volume so as to be able to accept gas displaced from a sealed vial when the prefill volume of medical liquid is injected into the vial.

In certain embodiments, a syringe for extracting a dose volume of a medical fluid from a sealed vial is disclosed. The syringe includes a plunger having a plunger tube having proximal and distal ends, a center tube coupled to the proximal end of the plunger tube and extending within the plunger tube toward the distal end, the center tube having a center passage, and a balloon disposed over the center tube and sealingly fixed to the proximal end of the plunger tube. The balloon and the plunger tube form a gas volume having a minimum gas capacity. The syringe also includes a barrel having a barrel tube having proximal and distal ends and an interior configured to accept a portion of the plunger, a tip fixedly coupled to the proximal end of the barrel tube, a post fixedly attached to the tip and extending within the barrel tube toward the distal end, the tip configured to partially extend into the center passage of the plunger, and a gas passage extending from a proximal end of the tip to the distal end of the post. The syringe is fully inserted into the barrel such that a liquid volume formed between the plunger and barrel is approximately zero and the gas volume contains a quantity of gas that is greater than or equal to a maximum liquid capacity of the liquid volume plus the minimum gas capacity.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 1A-1B are cross-sections of a barrel and a plunger of an exemplary syringe according to certain aspects of the present disclosure.

FIGS. 2A-2B are cross-sections of an exemplary syringe extracting a liquid from a vial according to certain aspects of the present disclosure.

FIGS. 4A-4B are cross-sections illustrating an exemplary vial adapter configured to be used with the exemplary syringe to access the contents of a vial according to certain aspects of the present disclosure.

DETAILED DESCRIPTION

Figure 3A:
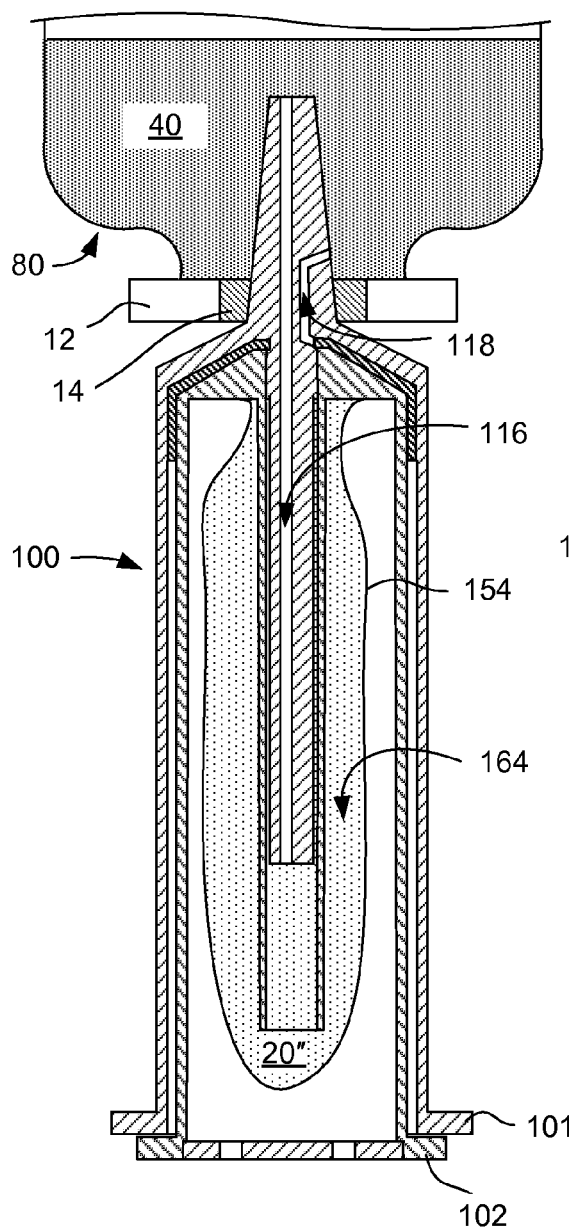
FIGS. 3A-3B are cross-sections of an exemplary syringe extracting a liquid from a vial according to certain aspects of the present disclosure.

The syringe disclosed herein is adapted for use with a sealed vial, in various embodiments, so as to maintain a generally constant pressure within the vial while adding or removing liquid. In certain embodiments, the disclosed syringe accepts a flow of gas from the vial that is displaced by liquid being introduced into the vial by the syringe and captures this displaced air, so as to prevent escape of the displaced air and any entrained medication into the ambient atmosphere. In certain embodiments, the disclosed syringe includes a reservoir of sterile air and provides a flow of this sterile air into the vial to replace liquid that is withdrawn from the vial by the syringe. The syringe may be used, in certain embodiments, directly with a vial or, in other embodiments, with a vial adapter configured to extend the liquid and gas passages of the syringe into the vial.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

While the discussion herein is directed to the use of the disclosed syringe to access the medical fluids with sealed vials, as typically provided in healthcare environments, this is a non-limiting example of how the disclosed syringe may be used. The same system and methods may be applied to other fields, for example the handling of radioactive liquids, wherein exposure of a user to the contents of a sealed container may present a risk.

Within this disclosure, the term "balloon" means a flexible, hollow element that has an interior with an opening wherein sealing the opening to a surface creates a sealed internal volume. The hollow element may be formed of an elastomeric material, which can stretch under an applied pressure, or a non-elastomeric material that does not stretch to a significant degree under an operational pressure. The balloon may be formed as an elongated cylinder with a closed end opposite to an opening but may, in certain embodiments, be provided in other shapes or forms, for example a sphere or as a flat sheet sealing a rigid enclosure. A balloon may have folds or pleats formed in a portion of the material.

FIGS. 1A-1B are cross-sections of a barrel 101 and a plunger 102 of an exemplary syringe 100 according to certain aspects of the present disclosure. As shown in FIG. 1A, the barrel 101 has a barrel tube 110 with an interior 111 open at a distal end. The tip 112 is fixedly coupled to and seals a proximal end of the barrel tube 110. In certain embodiments, the external surface 113 of the tip 112 has a conical form. In certain embodiments, the external surface 113 comprises a male Luer fitting. A post 114 is fixedly attached to a distal end of the tip 112 and extends within the barrel tube 110 toward the distal end. A gas passage 116 extends from a proximal end of the tip 112 to the distal end of the post 114. A liquid passage 118 extends from the interior of the barrel tube 110 to an exterior surface of the tip 112. In certain embodiments, the liquid passage 118 opens on the surface 113 proximate to the distal end of the surface 113. In certain embodiments, the distal end of the tip 112 is generally formed as a cone and the liquid passage 118 enters the interior of the barrel tube 110 at an inner edge of the conical end of the tip 112 such that all of a fluid within the interior of the barrel tube 110 may drain, when oriented as shown in FIG. 1, through the liquid passage 118.

FIG. 1B shown that the plunger 102 has a plunger tube 150 having an interior 151 open at a distal end and closed at a proximal end. A center tube 152 is fixedly coupled to the proximal end of the plunger tube 150 and extends within the plunger tube 150 toward the distal end. A center passage 162 extends from the distal end of the center tube 152 to the proximal end of the plunger 102 and is configured to allow the post 114 to slide within the center passage 162 when the plunger 102 is inserted into the barrel 101. A flexible balloon 154 is disposed over the center tube 152 and is sealingly fixed to the closed end of the plunger tube 150, thereby forming an interior gas volume 164. A vent cap 156 covers the distal end of the plunger tube 150 and has one or more vent holes 158 to allow ambient air to pass into or out of the interior 151 of the plunger tube 150 while protecting the balloon 154 from damage.

A sealing member 160 is formed on the proximal end of the plunger 102 and seals to the barrel 101. In certain embodiments, the proximal side of the sealing member 160 has a shape that is complementary to the conical shape of the distal end of the tip 112. The sealing member 160 sealingly engages the interior surface of the barrel tube 110 when the plunger 102 is inserted into the barrel 101 so as to define a liquid volume of the syringe 100, as is discussed further with respect to FIGS. 2A, 2B. The sealing member 160 also forms a seal with the post 114.

FIGS. 2A-2B are cross-sections of an exemplary syringe 100 injecting a liquid 10 into a vial 80 according to certain aspects of the present disclosure. The syringe 100 has a barrel 101 and a plunger 102 that generally are configured as discussed with respect to FIGS. 1A, 1B.

In FIG. 2A, the syringe 100 is shown with the tip 112 inserted though a septum 14 in the cap 12 of an example vial 80 that is used to illustrate the features of the syringe 100. In this example, the interior volume 16 of the vial 80 is partially filled with a powdered medication 30 and the remaining space is filled with a gas 32. For other types of vials having septums adapted for penetration by a needle, a vial adapter may be coupled to the vial 80 to provide a female needleless fitting suitable to accept the tip 112, as is discussed in greater detail with respect to FIGS. 4A, 4B. In certain embodiments, the tip 112 of the syringe 100 may have a needle (not shown in FIG. 2A) within one or both passages 116 and 118 passing through portions of the needle. Other arrangements of tips for obtaining access to the interior of a sealed vial of various types having liquid and gas passages arranged as disclosed herein will be apparent to those of skill in the art.

In FIG. 2A, the plunger 102 is partially inserted into the barrel 101 so as to form a liquid volume filled with a liquid 10, for example sterile water. The sealing member 160 forms a seal with the interior surface of the barrel tube 110 and with the post 114 to define this liquid volume. In this example, the balloon 154 has a minimum volume of the gas volume 164 and is filled with a sterile gas 20.

FIG. 2B depicts the syringe of FIG. 2A after the plunger 102 has been pushed in the proximal direction as indicated by the arrow "A" with respect to the barrel 101, thereby injecting a portion 10' of the liquid 10 through the liquid passage 118 into the vial 80, leaving a remaining portion 10". As the vial 80 is sealed, the volume 16 is fixed and addition of a non-compressible liquid would increase the pressure within the vial 80 if there was no path to vent a portion of the gas or liquid from the vial 80. With the exemplary syringe 100, the gas passage 116 allows a portion 32' of the gas 32 within the vial 80 to flow from the vial 80 into the interior 164 of the balloon 154. As the balloon 154 is expandable and exposed to the ambient environment through the vent holes 158, the pressures within the interior 164 of the balloon 154 and within the vial 80 remain approximately constant and at ambient pressure. Thus, the pressure within the vial 80 remains approximately at ambient pressure during the injection of the liquid 10 into the vial 80 to reconstitute the powdered medication 30.

A benefit of capturing the expelled portion 32' within a sealed volume 164 is that the user is not exposed to the contents of the vial 80. For certain medications, for example an oncology medication, the pure medication 30 may be toxic and the expelled portion 32' may entrain some of the medication 30 in either powdered or liquid form. Since the balloon 154 is sealed to the plunger tube 152 and expands as the portion 32' enters the volume 164 to produce a gas volume 20" within the balloon, none of the expelled portion 32' of the gas passes into the ambient environment. In certain embodiments, the balloon 154 is capable of expanding to a volume 164 that is greater than or equal to the minimum volume of the balloon 154 plus the maximum volume of liquid that the syringe 100 can contain.

Figure 3B:
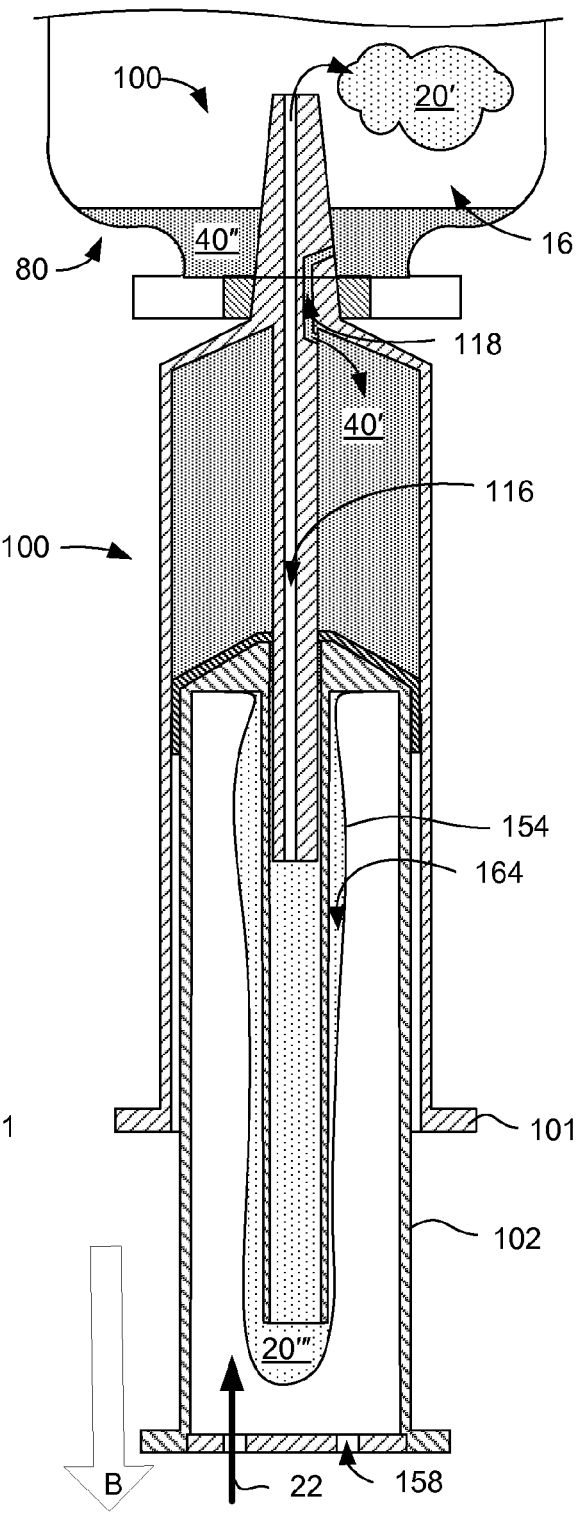

FIGS. 3A-3B are cross-sections of the exemplary syringe 100 of FIG. 1 extracting a liquid 40 from a vial 80 according to certain aspects of the present disclosure. In certain embodiments, the sequence of events depicted in FIGS. 3A, 3B may occur immediately after the powdered medication 30 is reconstituted with liquid 10 to form the liquid medication 40, as shown in the sequence of FIGS. 2A, 2B. In certain embodiments, a vial 80 may be provided with a liquid medication 40 and so the process may be initiated as shown in FIG. 3A.

In FIG. 3A, a syringe 100 is shown with the tip 112 inserted though a septum 14 in the cap 12 of an example vial 80, as discussed above with respect to FIG. 2A. The plunger 102 is, in this example, fully depressed within the barrel 101. The volume 164 within the balloon 154 contains a volume of gas 20" that, in this example, is the same as the volume of gas 20" within the volume 164 of FIG. 2B. In this example, the liquid volume within the syringe 100 in the configuration of FIG. 3A is approximately zero.

FIG. 3B depicts the syringe 100 after the plunger 102 has been withdrawn a certain distance from the barrel 101 as indicated by the arrow "B." A portion 40' of the liquid 40 has been drawn from the vial 80 through the liquid passage 118 and into the interior of the barrel 110, leaving a remainder 40" within the vial 80. As the liquid 40 leaves the vial 80, a partial vacuum is created within the vial 80 that draws a portion 20' of the gas 20" from the balloon 152 through the central passage 116 into the interior of the vial 80, leaving a remainder 20' in the gas volume 164. The pressure within the gas volume 164 of balloon 154 remains approximately at ambient pressure, since the balloon 154 is exposed to the ambient atmosphere through vent holes 158, and ambient air flows in, as indicated by arrow 22, as the volume 164 decreases. As the interior 16 of the vial 80 is connected through the gas passage 116 to the volume 164, the interior 16 also remains at approximately ambient pressure. The volume 164 may be sized to contain enough gas 20" to allow the full capacity of the syringe 100 to be drawn from the vial 80.

FIGS. 4A-4B are cross sections of an example vial adapter 200 configured for use with the syringe 100 according to certain aspects of the present disclosure. A needle 220 is fixed to a proximal side of the adapter 200. The needle 220 has two passages—a gas passage 225 and a liquid passage 230. The vial adapter 200 has a cavity 210 that is, in certain embodiments, configured as a female Luer fitting. The cavity 210 has a recess 235 that, in this example, extends around the cavity 210 at the location corresponding to the position of the opening of the liquid passage 118. This embodiment of recess 235 allows the syringe 100 to be oriented in any rotational position while maintaining fluid coupling of the recess 235 and the fluid passage 118. The recess 235 is connected to the liquid passage 230 and the gas passage 225 is connected to a proximal end of the cavity 210. The adapter 200 also has a capture feature 215 that is configured to engage a lid 12 of a sealed via 80, such as is known to those of skill in the art. In this example, the syringe 100 contains a liquid 40.

FIG. 4B depicts the vial adapter 200 engaged with a vial 80 and a syringe 100 coupled to the vial adapter 200. It can be seen that the gas passage 116 of the syringe 100 is coupled to the interior 16 of the vial 80 through the gas passage 225 and the liquid volume of the syringe 100 is coupled to the interior 16 of the vial 80 through the liquid passage 230. When held in an inverted position, as shown in FIG. 4B, the liquid 40 may be drawn into the liquid volume of the syringe 100 through the liquid passage 230 while gas passes from the syringe 100 through the gas passages 116 and 225 into the vial, as previously discussed with respect to FIGS. 3A, 3B.

It can be seen that the disclosed embodiments of the syringe provide the capability to inject a liquid into a sealed vial or to extract a liquid from a vial while maintaining the pressure within the vial at approximately ambient pressure. This reduces the effort required to inject or extract a liquid. In certain disclosed embodiments, the syringe reduces the risk of a user being exposed to a hazardous liquid contained in a vial by capturing the gas that is displaced from the vial when a liquid is introduced into the vial, for example to reconstitute a powdered medication. In certain disclosed embodiments, the syringe reduces the risk of contamination of the fluid in the vial by providing sterile gas into the vial from a reservoir within the syringe as liquid is drawn out of the vial, thereby avoiding the need to allow non-sterile ambient air into the vial.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

To the extent that the term "include," "have," or the like is used in the description or the claims, such term is intended to be inclusive in a manner similar to the term "comprise" as "comprise" is interpreted when employed as a transitional word in a claim.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A syringe comprising:
    a plunger comprising:
        a plunger tube having proximal and distal ends;
        a center tube coupled to the proximal end of the plunger tube and extending within the plunger tube toward the distal end, the center tube having a center passage; and
        a balloon disposed over the center tube and sealingly fixed to at least one of the center tube and the plunger tube; and
    a barrel comprising:
        a barrel tube having proximal and distal ends and an interior configured to accept a portion of the plunger;
        a tip fixedly coupled to the proximal end of the barrel tube;
        a post fixedly attached to the tip and extending within the barrel tube toward the distal end, the tip configured to partially extend into the center passage of the plunger; and
        a gas passage extending from a proximal end of the tip to the distal end of the post.

2. The syringe of claim 1, wherein the barrel further comprises a liquid passage between an exterior surface of the tip and the interior of the barrel tube.

3. The syringe of claim 1, wherein:
    the plunger and barrel form a liquid volume when the plunger is partially disposed within the barrel, the liquid volume varying between zero and a maximum liquid capacity; and
    the balloon and the at least one of the center tube and the plunger tube form an interior gas volume varying between a minimum gas capacity and a maximum gas capacity that is greater than or equal to the maximum liquid capacity plus the minimum gas capacity.

4. The syringe of claim 3, wherein the gas volume contains a sterile gas.

5. The syringe of claim 3, wherein the plunger is disposed within the barrel such that the liquid volume is approximately zero and the gas volume is greater than or equal to the maximum liquid capacity plus the minimum gas capacity.

6. The syringe of claim 3, wherein the plunger is disposed within the barrel such that the liquid volume contains a prefill volume of liquid and the balloon is able to further expand such that the gas volume further increases by at least the prefill volume.

7. The syringe of claim 1, wherein the tip comprises a male Luer fitting.

8. The syringe of claim 1, wherein the plunger further comprises a vent cap attached at the distal end, the vent cap having at least one vent hole.

9. The syringe of claim 1, wherein the plunger further comprises a sealing member attached at the proximal end, the sealing member having an external surface that sealingly engages an interior surface of the barrel tube when the plunger is inserted into the barrel so as to define the liquid volume of the syringe.

10. A pre-filled syringe containing a prefill volume of a medical fluid, the syringe comprising:
    a plunger comprising:
        a plunger tube having proximal and distal ends;
        a center tube coupled to the proximal end of the plunger tube and extending within the plunger tube toward the distal end, the center tube having a center passage; and
        a balloon disposed over the center tube and sealingly fixed to at least one of the center tube and the plunger tube, wherein the balloon and the at least one of the center tube and the plunger tube form a gas volume containing a gas; and
    a barrel comprising:
        a barrel tube having proximal and distal ends and an interior configured to accept a portion of the plunger;
        a tip fixedly coupled to the proximal end of the barrel tube;
        a post fixedly attached to the tip and extending within the barrel tube toward the distal end, the tip configured to partially extend into the center passage of the plunger; and
        a gas passage extending from a proximal end of the tip to the distal end of the post,
    wherein the plunger is partially inserted into the barrel so as to form a liquid volume that contains the prefill amount of the medical fluid, and
    wherein the balloon is able to further expand such that the gas volume increases by at least the prefill volume so as to be able to accept gas displaced from a sealed vial when the prefill volume of medical liquid is injected into the vial.

11. The pre-filled syringe of claim 10, wherein the barrel further comprises a liquid passage between an exterior surface of the tip and the interior of the barrel tube.

12. The pre-filled syringe of claim 10, wherein the tip comprises a male Luer fitting.

13. The pre-filled syringe of claim 10, wherein the plunger further comprises a vent cap attached at the distal end, the vent cap having at least one vent hole.

14. The pre-filled syringe of claim 10, wherein the plunger further comprises a sealing member attached at the proximal end, the sealing member having an external surface that sealingly engages an interior surface of the barrel tube when the plunger is inserted into the barrel so as to define the liquid volume of the syringe.

15. The pre-filled syringe of claim 10, wherein the gas volume contains a sterile gas.

16. A syringe for extracting a dose volume of a medical fluid from a sealed vial, the syringe comprising:
a plunger comprising:
a plunger tube having proximal and distal ends;
a center tube coupled to the proximal end of the plunger tube and extending within the plunger tube toward the distal end, the center tube having a center passage; and
a balloon disposed over the center tube and sealingly fixed to the proximal end of the plunger tube, wherein the balloon and the plunger tube form a gas volume having a minimum gas capacity; and
a barrel comprising:
a barrel tube having proximal and distal ends and an interior configured to accept a portion of the plunger;
a tip fixedly coupled to the proximal end of the barrel tube;
a post fixedly attached to the tip and extending within the barrel tube toward the distal end, the tip configured to partially extend into the center passage of the plunger; and
a gas passage extending from a proximal end of the tip to the distal end of the post,
wherein the syringe is fully inserted into the barrel such that a liquid volume formed between the plunger and barrel is approximately zero and the gas volume contains a quantity of gas that is greater than or equal to a maximum liquid capacity of the liquid volume plus the minimum gas capacity.

17. The syringe of claim 16, wherein the barrel further comprises a liquid passage between an exterior surface of the tip and the interior of the barrel tube.

18. The syringe of claim 16, wherein the tip comprises a male Luer fitting.

19. The syringe of claim 16, wherein the plunger further comprises a vent cap attached at the distal end, the vent cap having at least one vent hole.

20. The syringe of claim 16, wherein the plunger further comprises a sealing member attached at the proximal end, the sealing member having an external surface that sealingly engages an interior surface of the barrel tube when the plunger is inserted into the barrel so as to define the liquid volume of the syringe.

21. The syringe of claim 16, wherein the gas volume contains a sterile gas.

* * * * *